United States Patent [19]

Baldwin et al.

[11] Patent Number: 5,120,757
[45] Date of Patent: * Jun. 9, 1992

[54] SUBSTITUTED AROMATIC SULFONAMIDES AS ANTIGLAUCOMA AGENTS

[75] Inventors: John J. Baldwin, Gwynedd Valley; Gerald S. Ponticello, Lansdale, both of Pa.

[73] Assignee: Merck & Co., Inc., Rahway, N.J.

[*] Notice: The portion of the term of this patent subsequent to Aug. 7, 2007 has been disclaimed.

[21] Appl. No.: 387,034

[22] Filed: Jul. 31, 1989

[51] Int. Cl.⁵ .................. A61K 31/385; C07D 495/04
[52] U.S. Cl. ............................... 514/432; 514/222.2; 514/231.5; 514/321; 514/422; 544/61; 544/146; 546/197; 548/526; 549/23
[58] Field of Search ........................... 549/23; 514/432

[56] References Cited

U.S. PATENT DOCUMENTS 4,677,115 6/1987 Baldwin et al. ............... 514/432
4,797,413 1/1989 Baldwin et al. ............... 514/432
4,946,859 8/1990 Hoffman et al. ............... 514/432

Primary Examiner—Mary C. Lee
Assistant Examiner—Jacqueline Haley
Attorney, Agent, or Firm—Donald J. Perrella; Joseph F. DiPrima; William H. Nicholson

[57] ABSTRACT

Carbonic anhydrase inhibitors of the thieno[2,3-b]thiopyran-2-sulfonamide type with a substituted-alkyl-amino group in the 4-position are topically effective in lowering intraocular pressure.

5 Claims, No Drawings

SUBSTITUTED AROMATIC SULFONAMIDES AS ANTIGLAUCOMA AGENTS

SUMMARY OF THE INVENTION

This invention relates to novel aromatic sulfonamides useful in the treatment of elevated intraocular pressure. More particularly this invention relates to compounds having the structural formula:

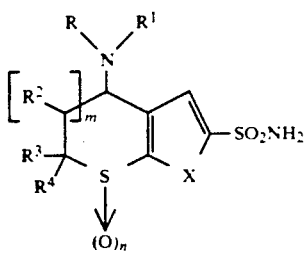

as well as the pharmaceutically and ophthalmologically acceptable salts thereof. This invention also relates to pharmaceutical compositions and the use thereof for systemic and ophthalmic use employing a novel compound of this invention as active ingredient for the treatment of elevated intraocular pressure, especially when accompanied by pathological damage such as in the disease known as glaucoma.

BACKGROUND OF THE INVENTION

Glaucoma is an ocular disorder associated with elevated intraocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many $\beta$-adrenergic blocking agents are effective in reducing intraocular pressure. While many of these agents are effective in reducing intraocular pressure, they also have other characteristics, e.g. membrane stabilizing activity, that are not acceptable for chronic ocular use. (S)-1-tert-Butylamino-[(4-morpholino-1,2,5-thiadiazol-3-yl)oxy]-2-propanol, a $\beta$-adrenergic blocking agent, was found to reduce intraocular pressure and to be devoid of many unwanted side effects associated with pilocarpine and, in addition, to possess advantages over many other $\beta$-adrenergic blocking agents, e.g. to be devoid of local anesthetic properties, to have a long duration of activity, and to display minimal tolerance.

Although pilocarpine, physostigmine and the $\beta$-blocking agents mentioned above reduce intraocular pressure, none of these drugs manifests its action by inhibiting the enzyme carbonic anhydrase and, thereby, impeding the contribution to aqueous humor formation made by the carbonic anhydrase pathway.

Agents referred to as carbonic anhydrase inhibitors block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of inhibiting carbonic anhydrase throughout the entire body. Such a gross disruption of a basic enzyme system is justified only during an acute attach of alarmingly elevated intraocular pressure, or when no other agent is effective. Despite the desirability of directing the carbonic anhydrase inhibitor only to the desired opthalmic target tissue, no topically effective carbonic anhydrase inhibitors are available for clinical use.

However, topically effective carbonic anhydrase inhibitors are reported in U.S. Pat. Nos. 4,386,098; 4,416,890; and 4,426,388. The compounds reported therein are 5 (and 6)-hydroxy-2-benzothiazolesulfonamides and acyl esters thereof.

More recently, U.S. Pat. Nos. 4,677,115 and 4,797,413 describe topically effective carbonic anhydrase inhibitors which are thiopyranothiophene-2-sulfonamides differing from the compounds of the present application in the nature of the substituent on the thiopyran moiety para to the sulfur atom.

DETAILED DESCRIPTION OF THE INVENTION

The novel compounds of this invention are those with structural formula:

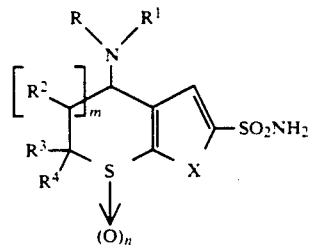

or a pharmaceutically acceptable salt thereof wherein:
X is —S—, or —O—;
m is 0, 1 or 2
n is 0, 1 or 2
R is hydrogen or $R^1$
$R^1$ is
1) $C_{2-7}$alkene,
2) $C_{2-7}$alkyne,
3) $C_{1-5}$alkyl having 1, 2 or 3 substituents wherein the substituents are independently:
   a) halogen, such as fluoro, chloro or bromo;
   b) hydroxy;
   c) —$NR^6R^7$ wherein $R^6$ and $R^7$ are independently:
      i) hydrogen,
      ii) $C_{1-3}$alkyl,
      iii) —CO—$C_{1-3}$alkyl, or
      iv) $R^6$ and $R^7$ taken together with the nitrogen to which they are attached represent a saturated heterocycle of 5–7 members which may include a second hetero group selected from O, S, SO, or $SO_2$ such as pyrrol-1-yl, piperidin-1-yl, 4-($C_{1-3}$alkyl)-piperidin-1-yl, morpholin-4-yl, thiomorpholin-1-yl and its oxide and dioxide, d) —S—$C_{1-3}$alkyl,
      |
      $(O)_n$ e) —CN, f) $C_{1-3}$ alkoxy,
g) —SH,
h) $C_{1-3}$ alkoxycarbonyl, i) 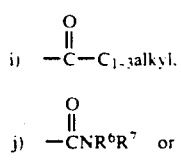

j) $-\overset{O}{\overset{\|}{C}}NR^6R^7$  or k) $C_{3-6}$ cycloalkyl;

$R^2$ is
1) hydrogen,
2) —CN,
3) phenyl-$C_{1-3}$-alkyl, wherein the phenyl is either unsubstituted or substituted with one or more of
   a) hydroxy,
   b) $C_{1-3}$-alkoxy,
   c) $R^6R^7N$-$C_{1-5}$alkyl, or
4) $C_{1-5}$-alkyl; and $R^3$ and $R^4$ are independently:
1) hydrogen,
2) $C_{1-5}$ alkyl, either unsubstituted or substituted with one or more of
   a) —$NR^8R^9$, wherein $R^8$ and $R^9$ are independently
      i) hydrogen,
      ii) $C_{1-5}$alkyl, either unsubstituted or substituted with phenyl, wherein the phenyl is either unsubstituted or substituted with $C_{1-3}$alkoxy, halo, such as fluoro, or chloro, or di($C_{1-3}$alkyl)amino;
   b) phenyl, either unsubstituted or substituted with one or more of
      i) hydroxy,
      ii) $C_{1-3}$ alkoxy, or
      iii) $C_{1-3}$ alkyl-$NR^{10}R^{11}$, wherein $R^{10}$ and $R^{11}$ are independently hydrogen, or $C_{1-5}$alkyl;
3) phenyl, either unsubstituted or substituted with
   i) hydroxy,
   ii) $C_{1-3}$alkoxy,
   iii) $C_{1-3}$alkyl-$NR^{10}R^{11}$,
   iv) halo,
4) aromatic heterocycle of 5 or 6 members such as furyl, pyridyl, or thienyl either unsubstituted or substituted with $C_{1-3}$alkyl-$NR^{10}R^{11}$; or $R^3$ and $R^4$ taken together represent methylene: with the proviso that $R^1$ is not 2-hydroxy-2-methyl-1-propyl if R, $R^2$, $R^3$ and $R^4$ are all hydrogen and n is 2.

It is preferred that R and $R^2$ are hydrogen, and that one of $R^3$ and $R^4$ is hydrogen or $C_{1-3}$alkyl while the other is $C_{1-3}$alkyl.

It is also preferred that $R^1$ is $C_{1-5}$alkyl substituted with hydroxy.

Compounds especially preferred are:
5,6-dihydro-4-(2-methoxy-2-ethylamino)-6-methyl-4H-thieno[2,3-b]thiopyran-2-sulfonamide-7,7-dioxide;
5,6-dihydro-4-(2-hydroxypropylamino)-4H-thieno[2,3-b]-thiopyran-2-sulfonamide-7,7-dioxide;
5,6-dihydro-4-(3-hydroxypropylamino)-4H-thieno[2,3-b]-thiopyran-2-sulfonamide; and
5,6-dihydro-4-(2-hydroxyethylamino)-4H-thieno[2,3-b]-thiopyran-2-sulfonamide.

The 4-substituted-alkylamino compounds of this invention are prepared from the corresponding 4-hydroxy compounds by treatment of the 4-hydroxy with toluenesulfonyl chloride in pyridine at about $-20°$ C. to 5° C. for about 3 to 10 hours followed by the addition of an alkylamine at a temperature below about 15° C. followed by warming to about 30°–60° C. for about 5 to 16 hours.

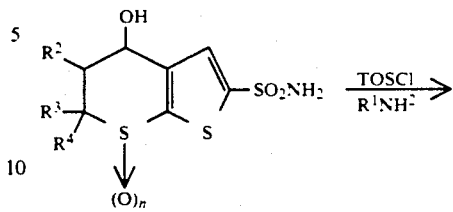

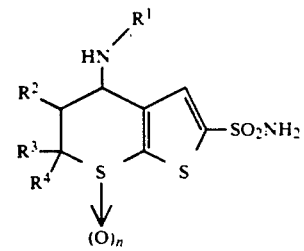

The novel pharmaceutical formulations of this invention are adapted for oral administration such as tablets, capsules or the like; for nasal administration, especially in the form of a spray; for injection, in the form of a sterile injectable liquid; or for topical ocular administration in the form of solutions, ointments, solid water soluble polymeric inserts, or gels.

This invention is particularly concerned with formulations adapted for topical ocular administration for the treatment of glaucoma and other stages of elevated intraocular pressure and contain about 0.1% to 15% by weight of medicament, especially about 0.5 to 2% by weight of medicament, the remainder being comprised of carriers and other excipients well known in the art.

The medicament in the novel topical ocular formulations comprises one of the novel compounds of this invention either alone or in combination with a β-adrenergic blocking agent such as timolol maleate or a parasympathomimetic agent such as pilocarpine. In such combinations the two active agents are present in approximately equal amounts.

The novel method of treatment of this invention comprises the treatment of elevated intraocular pressure by the administration of a novel compound of this invention or a pharmaceutical formulation thereof. Of primary concern is the treatment by topical ocular administration of about 0.1 to 25 mg and especially 0.2 to 10 mg of such compound per day, either by single dose or on a 2 to 4 dose per day regimen.

EXAMPLE 1

(α and β)

5,6-Dihydro-4H-4-(2-hydroxypropylamino)-thieno[2,3-b]thiopyran-2-sulfonamide-7,7-dioxide Under $N_2$, 5,6-dihydro-4H-4-hydroxythieno-[2,3-b]thiopyran-2-sulfonamide-7,7-dioxide (2.2 g, 7.8 mmol) in pyridine (12 ml) was cooled in an ice bath (4° C.) and p-toluenesulfonyl chloride (3.2 g, 16.8 mmol) was added portionwise with stirring. After 5 hours, 2-hydroxypropylamine (25 ml) was added at $-15°$ C. dropwise at a rate that the internal temperature did not exceed 15° C. After the addition, the reaction was stirred at room temperature for 2 hours and then at 50° C. for 15 hours. The volatiles were removed first at reduced pressure (20 mm) and then high vacuum (1 mm). The residue was treated with saturated NaHCO₃ and ethyl acetate, separated and further extracted with ethyl acetate (2X). The organic layers were dried, filtered and concentrated to dryness to yield 3.0 g of crude material. The residue was dry packed with silica gel and placed on a Still column (80 mm). The diastereomers were eluted from the column with 7.5% CH₃OH—CHCl₃ to yield 0.37 g (14%) of the α-isomer and 0.55 g (21%) of the β-isomer. The α-isomer was crystallized as the maleate salt, mp 182°–4° C. (CH₃OH—CH₃CN), and the β-isomer was crystallized as the hydrochloride salt, mp 258°–260° C.

(in PrOH). For the α-isomer analysis calc'd for $C_{10}H_{16}N_2O_5S_3.C_4H_4O_4$: Calc'd N, 6.18; C, 36.83; H, 4.42. Found N, 6.20; C, 36.75; H, 4.61. For the β-isomer analysis calc'd for $C_{10}H_{16}N_2O_5S_3.HCl$: Calc'd N, 7.43; C, 31.86; H, 4.55. Found N, 7.56; C, 31.82; H, 4.60.

Employing the procedure substantially as described in Example 1 but omitting the column chromatographic separation of diastereoisomers, if none are present, and merely crystallizing the product from a lower alkanol in the presence of lower alkanolic acid, there are produced the following compounds:

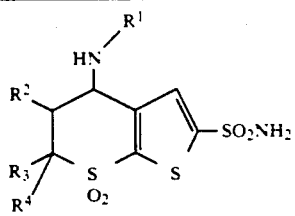

| $R^1$ | $R^2$ | $R^3$ | $R^4$ | isomer | m.p. (°C.) |
|---|---|---|---|---|---|
| —CH₂CH₂OH | H | H | H | | 213-216 (HCl) |
| —(CH₂)₃—OH | H | H | H | | 255-257 (HCl) |
| —CH₂C(CH₃)CH₃ | H | H | H | | 116-118 (HCl 0.25 C₃H₈O) |
| —CH₂C≡CH | H | H | H | | — |
| —CH₂CH₂CH₂F | H | H | H | | — |
| —CH₂CH₂CH₂OCH₃ | H | H | H | | — |
| —CH₂CH₂N(CH₃)₂ | H | H | CH₃ | α- | — |
| —CH₂CH₂N(CH₃)₂ | H | H | CH₃ | β- | — |
| —CH₂CH₂SH | H | H | H | | — |
| —CH₂CH₂SCH₃ | H | H | H | | — |
| —CH₂CH₂SO₂CH₃ | H | H | H | | — |
| —CH₂CH₂CN | H | H | H | | — |
| —CH₂CO₂C(CH₃)₃ | H | H | H | | — |
| —CH₂CH₂SCH₂CH₃ | H | H | CH₃ | α- | — |
| —CH₂CH₂SCH₂CH₃ | H | H | CH₃ | β- | — |
| —CH₂CH₂CH₂CH₃SO₂CH₃ | H | H | CH₃ | α- | — |
| —CH₂CH₂SO₂CH₂CH₃ | H | H | CH₃ | β- | — |
| —CH₂CH₂NCOCH₃<br>            \|<br>           CH₃ | H | H | H | | — |
| —CH₂CH₂N⟨pyrrolidine⟩ | H | H | H | | — |
| —CH₂CH₂N⟨piperidine⟩ | H | H | H | | — |
| —CH₂CH₂N⟨azepane⟩ | H | H | H | | — |
| —CH₂CH₂N⟨N-methylpiperazine⟩ | H | H | H | | — |
| —CH₂CH₂N⟨morpholine⟩ | H | H | H | | — |

-continued

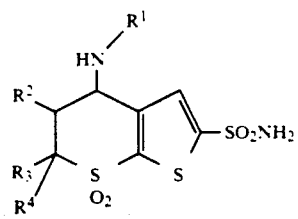

| R¹ | R² | R³ | R⁴ | isomer | m.p. (°C.) |
|---|---|---|---|---|---|
| —CH₂CH₂OH | H | H | p-CH₃OC₆H₄— | — | |
| —CH₂CH₂OH | H | furan-2-yl | H | — | |
| —CH₂CH₂OH | H | pyrid-2-yl | H | — | |
| —CH₂CH₂OH | H | H | thien-2-yl | — | |
| —CH₂CH₂OH | H | p-CH₃OC₆H₄—CH₂— | — | — | |
| —CH₂CH₂OH | —CN | H | H | — | |
| —CH₂CH₂OH | H | —CH₃ | —CH₃ | — | |
| —CH₂CH₂OH | H | H | —CH₂NHCH₂CH₃ | — | |
| —CH₂CH₂OH | H | H | —CH₂NH—⟨C₆H₄⟩—CH₃ | — | |
| —CH₂CH₂OH | H | H | —CH₂NH—⟨C₆H₄-Cl⟩ | — | |
| —CH₂CH₂OH | H | H | —CH₂NH—⟨C₆H₄⟩—N(CH₃)₂ | — | |
| —CH₂CH₂OH | H | H | ⟨furan⟩—CH₂NH(CH₃)₂ | — | |

EXAMPLE 2

| Active ingredient | 1 mg | 15 mg |
|---|---|---|
| Monobasic sodium phosphate 2H₂O | 9.38 mg | 6.10 mg |
| Dibasic sodium phosphate 12H₂O | 28.48 mg | 16.80 mg |
| Benzalkonium chloride | 0.10 mg | 0.10 mg |
| Water for injection q.s. and. | 1.0 ml | 1.0 ml |

The novel compound, phosphate buffer salts, and benzalkonium chloride are added to and dissolved in water. The pH of the composition is adjusted to 6.8 and diluted to volume. The composition is rendered sterile by ionizing radiation.

EXAMPLE 3

| Active ingredient | 5 mg |
|---|---|
| petrolatum q.s. and. | 1 gram |

The compound and the petrolatum are aseptically combined.

EXAMPLE 4

| Active ingredient | 1 mg |
|---|---|
| Hydroxypropylcellulose q.s. | 12 mg |

Ophthalmic inserts are manufactured from compression molded films which are prepared on a Carver Press by subjecting the powdered mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrate insert are then autoclaved at 250° F. for ½ hour.

What is claimed is:

1. A compound of structural formula:

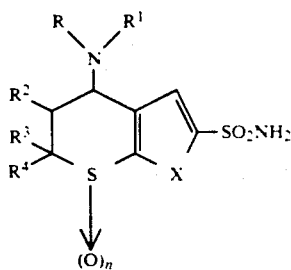

or a pharmaceutically acceptable salt thereof wherein:
X is —S—;
n is 0, 1 or 2;
R is hydrogen or $R^1$;
$R^1$ is
1) $C_{2-7}$-alkene,
2) $C_{2-7}$-alkyne,
3) $C_{1-5}$alkyl having 1, 2 or 3 substituents wherein the substituents are independently:
   a) halogen, or
   b) hydroxy;
$R^2$ is
1) hydrogen,
2) —CN,
3) phenyl-$C_{1-3}$ alkyl, wherein the phenyl is either unsubstituted or substituted with one or more of
   a) hydroxy,
   b) $C_{1-3}$-alkoxy,
   c) $R^6R^7NC_{1-5}$-alkyl-, wherein $R^6$ and $R^7$ are independently:

i) hydrogen,
ii) $C_{1-3}$alkyl,
iii) —CO—$C_{1-3}$alkyl, or
iv) $R^6$ and $R^7$ taken together with the nitrogen to which they are attached represent a saturated heterocycle of 5-7 members which may include a second hetero group selected from O, S, SO, or $SO_2$; or
4) $C_{1-5}$ alkyl; and $R^3$ and $R^4$ are independently:
1) hydrogen,
2) $C_{1-5}$ alkyl, unsubstituted;
with the proviso that $R^1$ is not 2-hydroxy-2-methyl-1-propyl if R, $R^2$, $R^3$ and $R^4$ are all hydrogen and n is 2.

2. The compound of claim 1 which is:
5,6-dihydro-4-(2-hydroxypropylamino)-4H-thieno[2,3-b]-thiopyran-2-sulfonamide-7,7-dioxide;
5,6-dihydro-4-(3-hydroxypropylamino)-4H-thieno[2,3-b]-thiopyran-2-sulfonamide;
5,6-dihydro-4-(2-hydroxyethylamino)-4H-thieno[2,3-b]-thiopyran-2-sulfonamide.

3. The compound of claim 1 wherein R and $R^2$ are hydrogen; $R^1$ is hydroxy-$C_{1-5}$-alkyl; and $R^3$ and $R^4$ are independently hydrogen or $C_{1-3}$-alkyl.

4. An ophthalmological formulation for the treatment of ocular hypertension comprising an ophthalmologically acceptable carrier and an effective ocular antihypertensive amount of a compound of claim 1.

5. A method of treating elevated intraocular pressure comprising the administration to a patient in need of such treatment of an effective intraocular pressure lowering amount of the compound of claim 1.

* * * * *